US011172891B2

(12) United States Patent
Aung et al.

(10) Patent No.: US 11,172,891 B2
(45) Date of Patent: Nov. 16, 2021

(54) METHOD AND APPARATUS FOR DERIVING MEAN ARTERIAL PRESSURE OF A SUBJECT

(71) Applicant: Nitto Denko Corporation, Osaka (JP)

(72) Inventors: Aye Aung, Singapore (SG); Kittipong Kasamsook, Singapore (SG); Visit Thaveeprungsriporn, Singapore (SG)

(73) Assignee: Nitto Denko Corporation

( * ) Notice: Subject to any disclaimer, the term of this patent is extended or adjusted under 35 U.S.C. 154(b) by 263 days.

(21) Appl. No.: 15/548,012

(22) PCT Filed: Dec. 23, 2015

(86) PCT No.: PCT/SG2015/050502
§ 371 (c)(1),
(2) Date: Aug. 1, 2017

(87) PCT Pub. No.: WO2016/130083
PCT Pub. Date: Aug. 18, 2016

(65) Prior Publication Data
US 2018/0020991 A1 Jan. 25, 2018

(30) Foreign Application Priority Data

Feb. 9, 2015 (WO) ................ PCT/SG2015/000034

(51) Int. Cl.
*A61B 5/00* (2006.01)
*A61B 5/021* (2006.01)
*A61B 5/024* (2006.01)

(52) U.S. Cl.
CPC ............ *A61B 5/7278* (2013.01); *A61B 5/002* (2013.01); *A61B 5/021* (2013.01);
(Continued)

(58) Field of Classification Search
CPC .... A61B 5/7278; A61B 5/021; A61B 5/02416
See application file for complete search history.

(56) References Cited

U.S. PATENT DOCUMENTS

| 4,889,133 A | 12/1989 | Nelson et al. |
| 5,776,071 A | 7/1998 | Inukai et al. |

(Continued)

FOREIGN PATENT DOCUMENTS

| CA | 1187721 A | 5/1985 |
| CN | 1925785 A | 3/2007 |

(Continued)

OTHER PUBLICATIONS

Katz ED, Ruoff BE. "Commonly Used Formulas and Calculations." In: Roberts: Clinical Procedures in Emergency Medicine. 4th ed. Elsevier Mosby Publishing;pp. 28-54; 1640-1651 (Year: 2004).*

(Continued)

*Primary Examiner* — Jonathan Cwern
*Assistant Examiner* — Amal Aly Farag
(74) *Attorney, Agent, or Firm* — Lerner, David, Littenberg, Krumholz & Mentlik, LLP

(57) ABSTRACT

A method and related apparatus for deriving mean arterial pressure of a subject, including receiving data relating to at least one cardiac cycle of a bio-signal from the subject; normalizing the received data relating to the at least one cardiac cycle; calculating an area enclosed by the normalized received data to obtain a normalized area; calculating a heart rate of the subject from the at least one cardiac cycle; and deriving the mean arterial pressure from the normalized area and heart rate.

17 Claims, 9 Drawing Sheets

(52) U.S. Cl.
CPC ...... *A61B 5/02116* (2013.01); *A61B 5/02416* (2013.01); *A61B 5/742* (2013.01); *A61B 5/6898* (2013.01)

(56) References Cited

U.S. PATENT DOCUMENTS

| | | | |
|---|---|---|---|
| 6,027,455 | A | 2/2000 | Inukai et al. |
| 6,623,443 | B1* | 9/2003 | Polaschegg ......... A61M 1/3639 604/5.04 |
| 8,463,347 | B2 | 6/2013 | Watson et al. |
| 2005/0119578 | A1 | 6/2005 | Kubo |
| 2007/0055163 | A1* | 3/2007 | Asada ................. A61B 5/02225 600/485 |
| 2008/0183232 | A1 | 7/2008 | Voss et al. |
| 2009/0204012 | A1 | 8/2009 | Joeken |
| 2010/0069764 | A1 | 3/2010 | Kang |
| 2011/0082357 | A1* | 4/2011 | Hornick ............. A61B 5/14551 600/364 |
| 2011/0196245 | A1* | 8/2011 | Poupko ................ A61B 5/4839 600/506 |
| 2011/0319724 | A1* | 12/2011 | Cox .................. A61B 5/02028 600/301 |
| 2012/0078125 | A1 | 3/2012 | Gornik et al. |
| 2013/0253341 | A1 | 9/2013 | Sethi et al. |
| 2015/0272512 | A1 | 10/2015 | Chen et al. |

FOREIGN PATENT DOCUMENTS

| | | |
|---|---|---|
| CN | 101502414 A | 8/2009 |
| CN | 101801264 A | 8/2010 |
| CN | 103327886 A | 9/2013 |
| CN | 103505191 A | 1/2014 |
| CN | 103767693 A | 5/2014 |
| JP | S57145641 A | 9/1982 |
| JP | H05207980 A | 8/1993 |
| JP | H11318837 A | 11/1999 |
| WO | 2005055825 A1 | 6/2005 |
| WO | 2009099833 A2 | 8/2009 |
| WO | 2012099537 A1 | 7/2012 |

OTHER PUBLICATIONS

Introduction to Biostatistics Course 704, "Multiple Linear Regression Analysis: Mutlivariable Methods." Boston University School of Public Health, Jan. 17; http://sphweb.bumc.bu.edu/otlt/MPH-Modules/BS/BS704_Multivariable/BS704_Multivariable7.html (Year : 2013).*

Razminia M, Trivedi A, Molnar J, Elbzour M, Guerrero M, Salem Y, et al. "Validation of a new formula for mean arterial pressure calculation: the new formula is superior to the standard formula". Catheter Cardiovasc Interv; 63:419-425 (Year: 2004).*

International Search Report for Application No. PCT/SG2015/050502, dated Jan. 27, 2016.

Raamat, R. et al, "Accuracy of some algorithms to determine the oscillometric mean arterial pressure: A theoretical study", Blood Pressure Monitoring, Feb. 2013, pp. 50-56, p. 52, vol. 18, No. 1, Lippincott Williams & Wilkins.

Search Report from Office Action for Chinese Application No. 2015800758182 dated Dec. 4, 2019; 2 pages.

* cited by examiner

METHOD AND APPARATUS FOR DERIVING MEAN ARTERIAL PRESSURE OF A SUBJECT

CROSS REFERENCE TO RELATED APPLICATIONS

The present application is a national phase entry under 35 U.S.C. § 371 of International Application No. PCT/SG2015/050502, filed Dec. 23, 2015, published in English, which claims priority to International Application No. PCT/SG2015/000034, filed Feb. 9, 2015, the disclosures of which are incorporated by reference herein.

FIELD

The present invention relates to a method and apparatus for deriving mean arterial pressure of a subject.

BACKGROUND

Arterial blood pressure measurements provide valuable information about a patient's cardiovascular system. A normal cardiovascular system is characterised by sufficient flow of blood to all parts of the patient's body, without producing prolonged strain on the physical capabilities of various organs through which the blood flows. In an abnormal cardiovascular system, blood pressure may be too high or too low, with each abnormality having attendant consequences for various body parts. The resultant prolonged strain may lead to heart, liver and kidney diseases and/or other complications. The importance of arterial blood pressure has thus spurred development of numerous methods for determining it.

Currently, the auscultation and oscillometric techniques are the most widely used techniques for measuring blood pressure. Blood pressure is determined based on a relationship between arterial pulsations and an external applied pressure. An air pump and an inflatable cuff are typically required, but however giving rise to two main disadvantages from the cuff based pressure monitoring systems. Firstly, the system may be too bulky and not easily portable for continuous blood pressure monitoring. Secondly, the inflated cuff may cause pain or discomfort to the patient, which consequently affects accuracy of blood pressure readings.

More advanced blood pressure monitoring systems that provide cuff-less measurement are typically based on utilisation of photoplethysmography (PPG) and/or electrocardiogram (ECG) signals. Features such as pulse transit time (PTT) and pulse arrival time (PAT) are extracted from the signals to determine a blood pressure. For measurement, multiple sensing devices are attached to different parts of a patient's body, which undesirably create discomfort to the patient, and is also troublesome to use. Further, these techniques may require pre-calibration procedures to obtain a patient-specific baseline relationship between the said features and blood pressure prior to initial use.

It is also appreciated that many conventional methods that analyse the arterial waveform signals are unable to achieve optimal results for older subjects. This problem is largely inherent from use of the dicrotic notch and the diastolic peak features within an arterial waveform. Briefly, the arterial waveform at any point along the arteries is a summation of incident and reflected waves: the incident wave travelling from the heart to a periphery site, and the reflected wave travelling back from the periphery site of wave reflection to the heart. In younger subjects, where arteries are distensible, a velocity of the pulse wave is relatively low. But for older subjects however, their arteries are stiffer due to age and so a velocity of the pulse wave is high, resulting in that the reflected wave returns faster, thus causing the interval between the systolic and diastolic peaks to decrease. From summation of the waves, the dicrotic notch and the diastolic peak of the pulse wave thus become less visually distinguishable. This effect is evidently seen from FIG. 8. With base reference to a 29 years old test subject (i.e. see systolic peak 902, diastolic peak 914 and dicrotic notch 908), it may be observed from FIG. 8 that in older subjects the dicrotic notch (i.e. see features labelled as 910 and 912) as well as diastolic peak (i.e. see features labelled as 916 and 918) indeed become much less visually distinguishable with increasing age.

One object of the present invention is therefore to address at least one of the problems of the prior art and/or to provide a choice that is useful in the art.

SUMMARY

According to a $1^{st}$ aspect of the invention, there is provided a method of deriving mean arterial pressure of a subject, the method comprising: (i) receiving data relating to at least one cardiac cycle of a bio-signal from the subject; (ii) normalizing the received data relating to the at least one cardiac cycle; (iii) calculating an area enclosed by the normalized received data to obtain a normalized area; (iv) calculating a heart rate of the subject from the at least one cardiac cycle; and (v) deriving the mean arterial pressure from the normalized area and heart rate.

An advantage of the proposed method is that using the normalized area and heart rate makes it much easier and more accurate to derive the mean arterial pressure of the subject, which does away with the need to determine the dicrotic notch and/or the diastolic peak which are difficult to determine.

Preferably, wherein the data relates to a plurality of cardiac cycles, and the method may include normalizing respective data relating to each of the cardiac cycles; calculating respective areas enclosed by respective normalized data to obtain respective normalized areas; and obtaining an average normalized area from the calculated normalized areas as the normalized area.

Preferably, the method may further include calculating respective heart rates from respective pairs of the cardiac cycles that are arranged consecutively; and obtaining an average heart rate from the respective heart rates as the heart rate.

Preferably, wherein the at least one cardiac cycle may include a pair of cardiac cycles, and wherein calculating the heart rate may include calculating the heart rate according to the equation: $HR=60/T$, where HR is the heart rate; and T is a time period determined between respective consecutive systolic peaks of the pair of cardiac cycles that are arranged consecutively.

Preferably, wherein calculating the heart rate may include calculating the heart rate according to the equation: $HR=60/T$, where HR is the heart rate; and T is a time period determined between respective consecutive valleys of the at least one cardiac cycle.

Preferably, wherein deriving the mean arterial pressure may include deriving the mean arterial pressure according to the equation: $\log(MAP)=b+a_1 \log(A)+a_2 \log(HR)$, where MAP is the mean arterial pressure; A is the normalized area; HR is the heart rate; and $a_1$, $a_2$, and b are predetermined constants.

Preferably, wherein calculating the area enclosed by the normalized received data may include calculating the area with respect to a time axis which defines the at least one cardiac cycle.

Preferably, wherein the received data relating to the at least one cardiac cycle may include a waveform signal thereof, and wherein normalizing the received data may include subtracting a minimum value of the waveform signal from the waveform signal to obtain a subtracted signal, and dividing the subtracted signal by a maximum value of the subtracted signal.

Preferably, the method may further comprise obtaining pulse pressure of the subject; and deriving systolic blood pressure and diastolic blood pressure of the subject according to the respective equations: DBP=MAP−(⅓) PP, and SBP=MAP+(⅔) PP, where MAP is the mean arterial pressure; DBP is the diastolic blood pressure; SBP is the systolic blood pressure; and PP is the pulse pressure.

According to a $2^{nd}$ aspect of the invention, there is provided a computer program for deriving mean arterial pressure of a subject, the computer program downloadable to an electronic device and includes a set of instructions, when executed, is arranged to control a processor of the electronic device to: (i) receive data relating to at least one cardiac cycle of a bio-signal from the subject; (ii) normalize the received data relating to the at least one cardiac cycle; (iii) calculate an area enclosed by the normalized received data to obtain a normalized area; (iv) calculate a heart rate of the subject from the at least one cardiac cycle; and (v) derive the mean arterial pressure from the normalized area and heart rate.

Preferably, the computer program may be downloadable over the internet.

According to a $3^{rd}$ aspect of the invention, there is provided a computer program stored in a memory of an electronic device, the computer program having a set of instructions, when executed, is arranged to control a processor of the electronic device to: (i) receive data relating to at least one cardiac cycle of a bio-signal from a subject; (ii) normalize the received data relating to the at least one cardiac cycle; (iii) calculate an area enclosed by the normalized received data to obtain a normalized area; (iv) calculate a heart rate of the subject from the at least one cardiac cycle; and (v) derive mean arterial pressure of the subject from the normalized area and heart rate.

According to a $4^{th}$ aspect of the invention, there is provided an apparatus for deriving mean arterial pressure of a subject, the apparatus comprising: (i) a receiver for receiving data relating to at least one cardiac cycle of a bio-signal from the subject; (ii) a processor for: (a) normalizing the received data relating to the at least one cardiac cycle; (b) calculating an area enclosed by the normalized received data to obtain a normalized area; (c) calculating a heart rate of the subject from the at least one cardiac cycle; and (d) deriving the mean arterial pressure from the normalized area and heart rate.

An advantage of the proposed apparatus is being able to acquire the bio-signal from a single measurement site (of the subject) without requiring an inflatable cuff, or needing patient-specific calibration prior to initial use. In addition, there is no need to identify the dicrotic notch and/or the diastolic peak in order to determine the mean arterial pressure.

Preferably, the apparatus may be in the form of an electronic device.

Preferably, the electronic device may be a telecommunications device or an optical measurement device.

Preferably, the apparatus may include an optical measurement device and a telecommunications device having the receiver; and wherein the optical measurement device may include a signal sensing device for obtaining the bio-signal from the subject, and a data processing module for determining data relating to the bio-signal, wherein the receiver of the telecommunications device may be arranged to receive the determined data of the bio-signal.

According to a $5^{th}$ aspect of the invention, there is provided a method of deriving mean arterial pressure of a subject, the method comprising: (i) receiving data relating to at least one cardiac cycle of a bio-signal from the subject; and (ii) deriving the mean arterial pressure according to the equation: $\log (MAP)=b+a_1 \log (X_1)+a_2 \log (X_2)+ \ldots +a_{n-1} \log (X_{n-1})+a_n \log (X_n)$, where MAP is the mean arterial pressure; $X_1$ to $X_n$ are respectively values of physiological features of the subject and/or arterial waveform features based on the received data; and $a_1$ to $a_n$, and b are predetermined constants.

Preferably, the physiological features may be selected from the group consisting of heart rate, respiratory rate, heart rate variability, blood pressure and pulse pressure.

Preferably, the received data may relate to the at least one cardiac cycle includes a waveform signal thereof, and the arterial waveform features may be selected from the group consisting of a waveform feature derived from at least one data point on the waveform signal, an area under the waveform signal, a frequency value and a kurtosis value obtained from a Power Spectral Density graph of the waveform signal.

Preferably, the method may further comprise normalizing the received data relating to the at least one cardiac cycle.

It should be apparent that features relating to one aspect of the invention may also be applicable to the other aspects of the invention.

These and other aspects of the invention will be apparent from and elucidated with reference to the embodiments described hereinafter.

BRIEF DESCRIPTION OF THE DRAWINGS

Embodiments of the invention are disclosed hereinafter with reference to the accompanying drawings, in which:

FIGS. 5a and 5b, shows a PPG signal prior and subsequent to normalization for determination of an area enclosed by a waveform of the signal being analysed;

FIGS. 6a to 6c, shows another PPG signal prior and subsequent to normalization for determination of an area enclosed by a waveform of the signal being analysed;

DETAILED DESCRIPTION OF PREFERRED EMBODIMENTS

Figure 1:
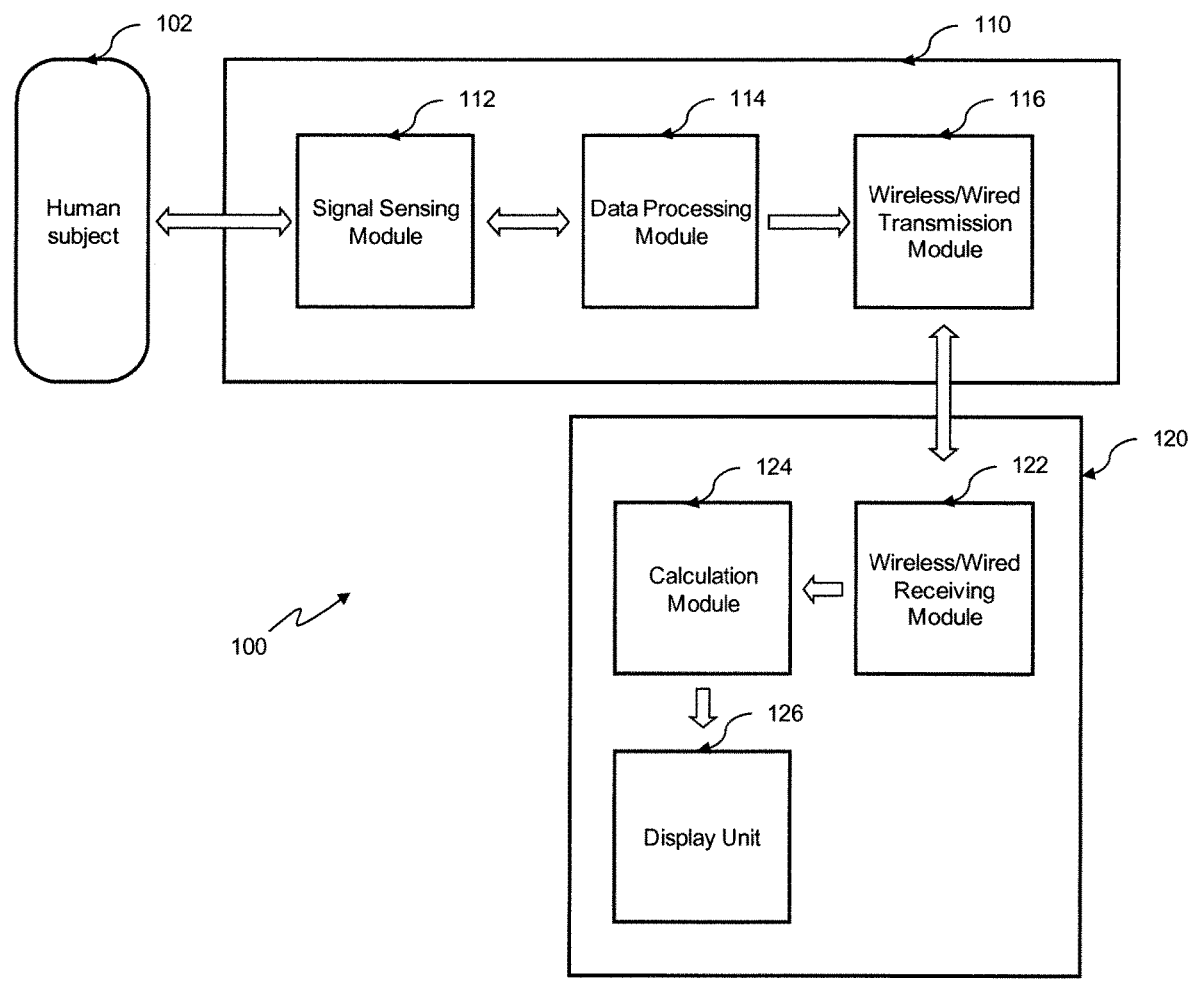
FIG. 1 is a schematic block diagram of an apparatus for measuring the blood pressure of a subject, based on a first embodiment of the invention.

FIG. 1 is a schematic block diagram of an apparatus 100 for measuring blood pressure of a (human) subject 102 according to a first embodiment. In particular, measuring blood pressure herein refers to deriving mean arterial pressure of the subject 102. The apparatus 100 includes an optical measurement device 110 comprising a signal sensing module 112 for obtaining a bio-signal from the said subject 102. The optical measurement device 110 further includes a data processing module 114 (e.g. such as a processor) which is arranged to receive and process the bio-signal from the signal sensing module 112, and a wireless/wired transmission module 116 for transmitting data processed from the bio-signal. It is to be appreciated that the optical measurement device 110 is preferably arranged to be conveniently portable, for example in a palm-sized form factor.

The transmission module 116 of the optical measurement device 110 is arranged to communicate wirelessly/non-wirelessly with a telecommunications device 120 such as a mobile phone or other portable electronic devices. The telecommunications device 120, which is included as the apparatus 100, includes a receiving module 122 for receiving signals from the optical measurement device 110, a calculation module 124 (which may be in the form of a processor) and a display unit 126 for displaying a result or information to a user of the apparatus 100. Of course, the receiver 122 is configured to receive the signals from the optical measurement device 110 wired/wirelessly, depending on the corresponding setup of the transmission module 116 of the optical measurement device 110.

Figure 2:
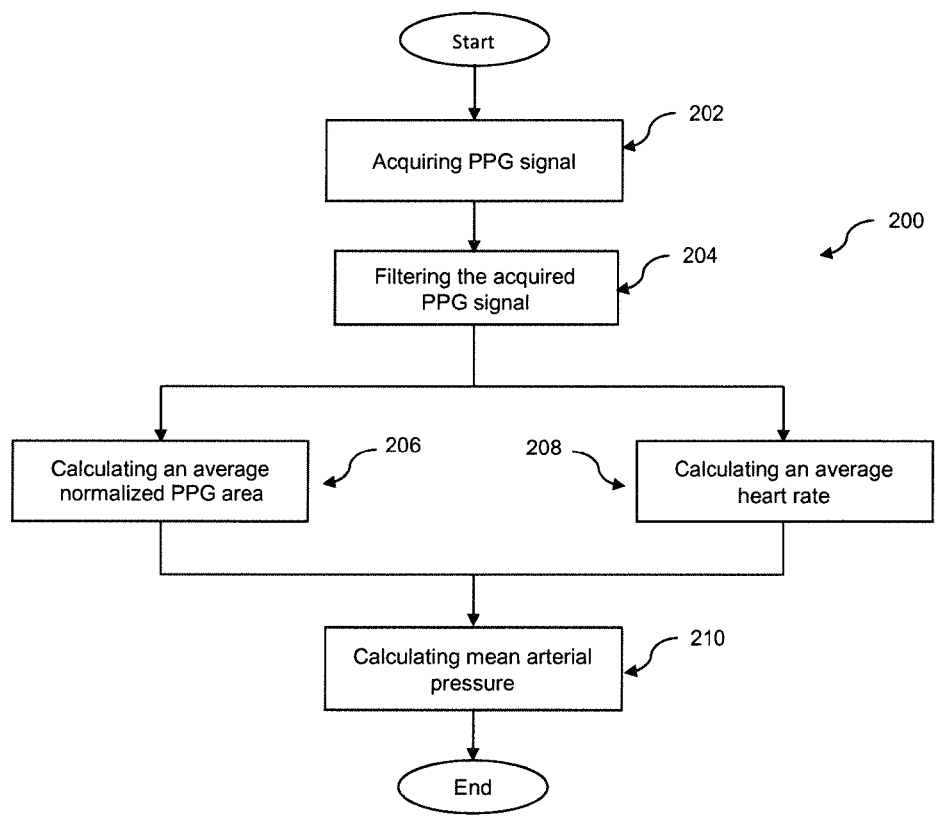
FIG. 2 is a flow diagram of a method, performed by the apparatus of FIG. 1, for deriving mean arterial pressure of the subject.

FIG. 2 is a flow diagram 200 of a method for deriving mean arterial pressure (MAP) of the subject 102, in which said method is performed by the apparatus 100 of FIG. 1. For good order, the importance of MAP is briefly explained here—MAP is defined as the average arterial pressure in an individual during one cardiac cycle and is a useful indicator of perfusion in vital organs. In particular, a MAP value of 60 mmHg or greater is required to maintain adequate tissue perfusion, and if the MAP value falls below 60 mmHg for an appreciable time, organs in the body will then be starved of oxygen, resulting in ischemia.

Figure 3:
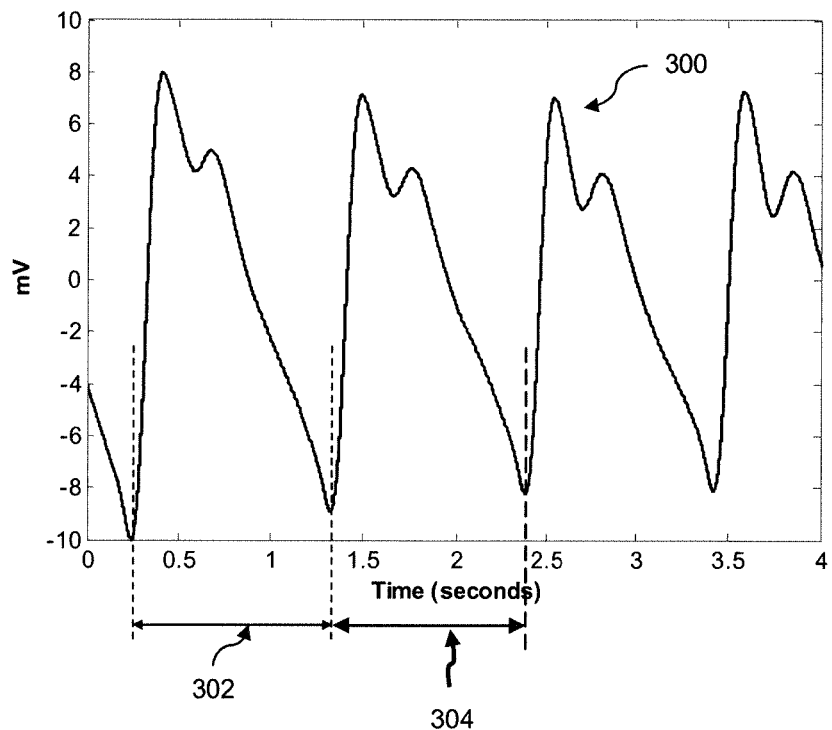
FIG. 3 is a diagram of a PPG signal having at least a cardiac cycle.

A brief overview of steps of the method (of FIG. 2) is first described, with detailed description of each step to follow further below. At step 202, signal acquisition is performed to obtain a bio-signal signal from the subject 102, and next at step 204, the acquired bio-signal is then filtered. It is to be appreciated that in this embodiment, the bio-signal is an arterial PPG waveform signal 300 comprising at least one cardiac cycle 302, 304, for example as depicted in FIG. 3. But in other variant embodiments, it is however to be appreciated that a pair (or a plurality) of cardiac cycles 302, 304 (as per FIG. 3) may also be utilised and the pair of cardiac cycles 302, 304 are arranged consecutively together (i.e. also see FIG. 7). At step 206, a normalized area is also calculated from the at least one cardiac cycle 302, 304, while at step 208, a heart rate of the subject 102 is calculated from the at least one cardiac cycle 302, 304. Finally, at step 210, a mean arterial pressure of the subject 102 is derived from collectively the calculated normalized area and heart rate using a proposed equation (4). It is to be appreciated that steps 206, 208 may be performed by the apparatus 100 sequentially or in parallel, depending on a specific intended implementation.

The above mentioned steps 202-210 of the method in FIG. 2 are now respectively described in greater detail as set out below.

1. Step 202 of the Method

At step 202, signal acquisition is performed by the optical measurement device 110 using the signal sensing module 112 to obtain the bio-signal from the subject 102 and as already mentioned, the bio-signal is the arterial PPG waveform signal 300 (hereinafter "PPG signal" for brevity) shown in FIG. 3. The PPG signal 300 may be acquired from any peripheral sites of a subject's body such as wrist and/or finger. It has been empirically determined that an accuracy suitable for calculating the subject's blood pressure may for example, but without being limiting, be achieved by configuring the signal sensing module 112 to employ a measurement window of at least 30 seconds to obtain the subject's bio-signal.

2. Step 204 of the Method

Figure 4:
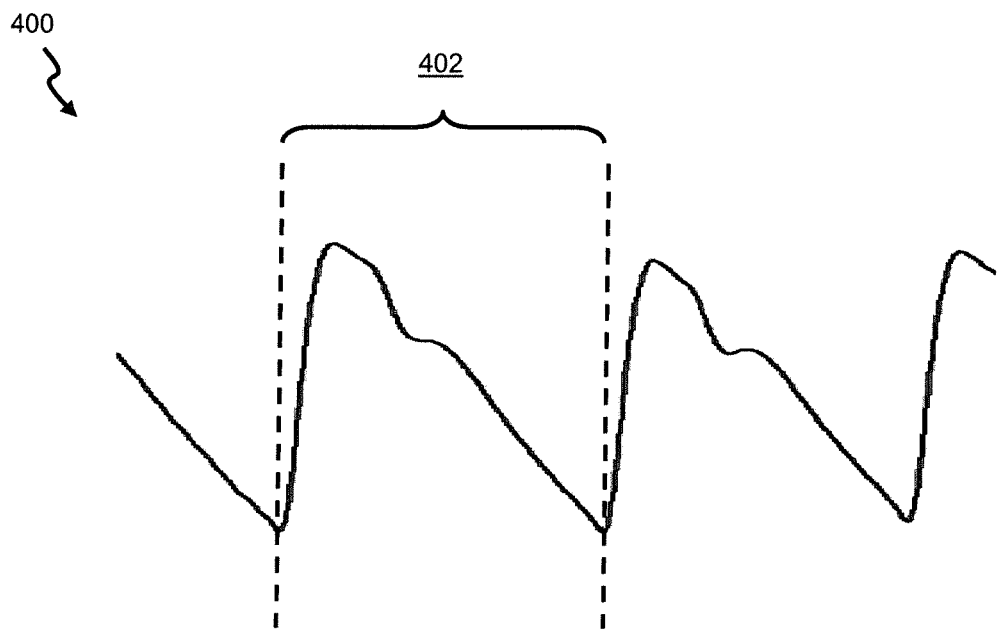
FIG. 4 is a diagram of a filtered PPG signal.

The acquired PPG signal 300 is next passed to the data processing module 114 for processing at step 204. The data processing module 114 may include a predefined digital band pass filter (not shown) for filtering any noise and signal artifacts present in the acquired PPG signal 300 to thereby provide a filtered PPG signal (not shown). In this case, reference to the filtered PPG signal will instead be made to FIG. 4 as the filtered PPG signal 400.

3. Step 206 of the Method

At step 206, the data processing module 114 calculates a normalized area of at least one cardiac cycle, although this does not preclude usage of a plurality of cardiac cycles (to be explained below). In this embodiment, the data processing module 114 is configured to calculate an area of a (selected) cardiac cycle 402 (i.e. with reference to FIG. 4) by applying a suitable mathematical function (e.g. an integration operation) to a (graphical) area enclosed by the waveform. It is of course to be appreciated that calculating the associated area enclosed by the cardiac cycle 402 is with respect to a time axis which defines the cardiac cycle 402. Alternatively, the data processing module 114 may also calculate the said area by comparing a shape of the area of the waveform to an approximately similar known shape (e.g. triangle, trapezoid, rectangle, circle or the like) from which area can subsequently be estimated and/or computed. Simply for information, an example of using the trapezoid rule or light weight computation method for calculating an area enclosed by a cardiac cycle is discussed in a patent publication WO2012/134,395. It is to be appreciated that the amplitude of each cardiac cycle waveform varies due to unavoidable minute changes in pressure applied between the signal sensing module 112 and a measurement site on the subject 102 (which arises from inherent minute body movement thereof). So in order to eliminate any amplitude difference(s) that arises from deviations in the applied pressure, a normalization step is performed by the data processing module 114. Specifically, each cardiac cycle waveform signal is normalized by first subtracting the minimum value of the signal from the signal to obtain a subtracted signal, which is then divided by the maximum value of the subtracted signal.

Figure 5:
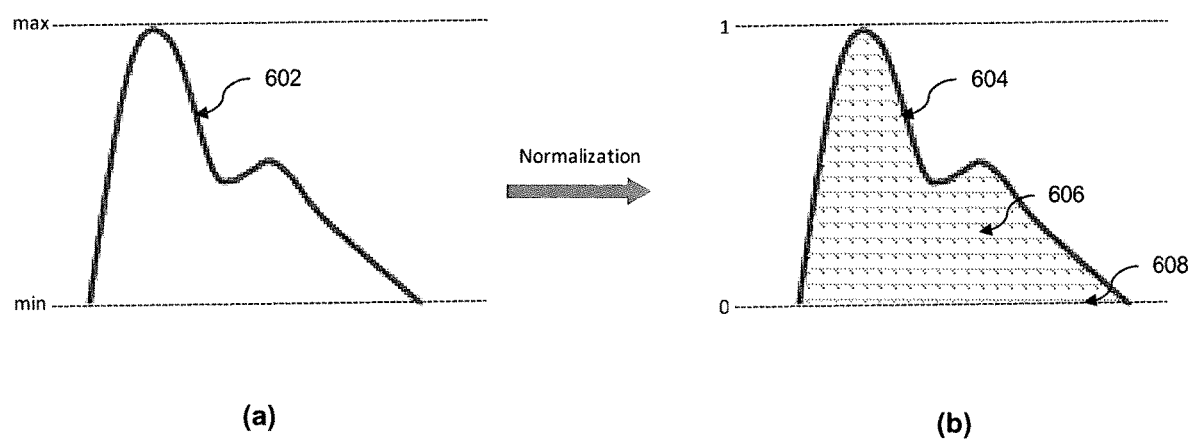
FIG. 5, which includes

As an example illustration, FIG. 5a shows a waveform signal 602 prior to normalization while FIG. 5b shows the same waveform (which is instead labelled as 604 to differentiate from FIG. 5a for easy explanation) subsequent to normalization (i.e. normalized waveform 604). In FIG. 5b, an area 606 under the normalized waveform 604 is then to be calculated by the data processing module 114. In this case, the area 606 is an area computed relative to a time axis 608, which is to be used as the normalized area.

That is, the PPG signal (e.g. the filtered PPG signal 400) is first normalized prior to calculating a graphical area enclosed by the normalized PPG signal to obtain an associated normalized area—i.e. data (or bio-signal) relating to at least one cardiac cycle (of the bio-signal) is normalized, and then a graphical area enclosed by the normalized data (or bio-signal) is calculated accordingly to arrive at the normalized area.

Figure 6:
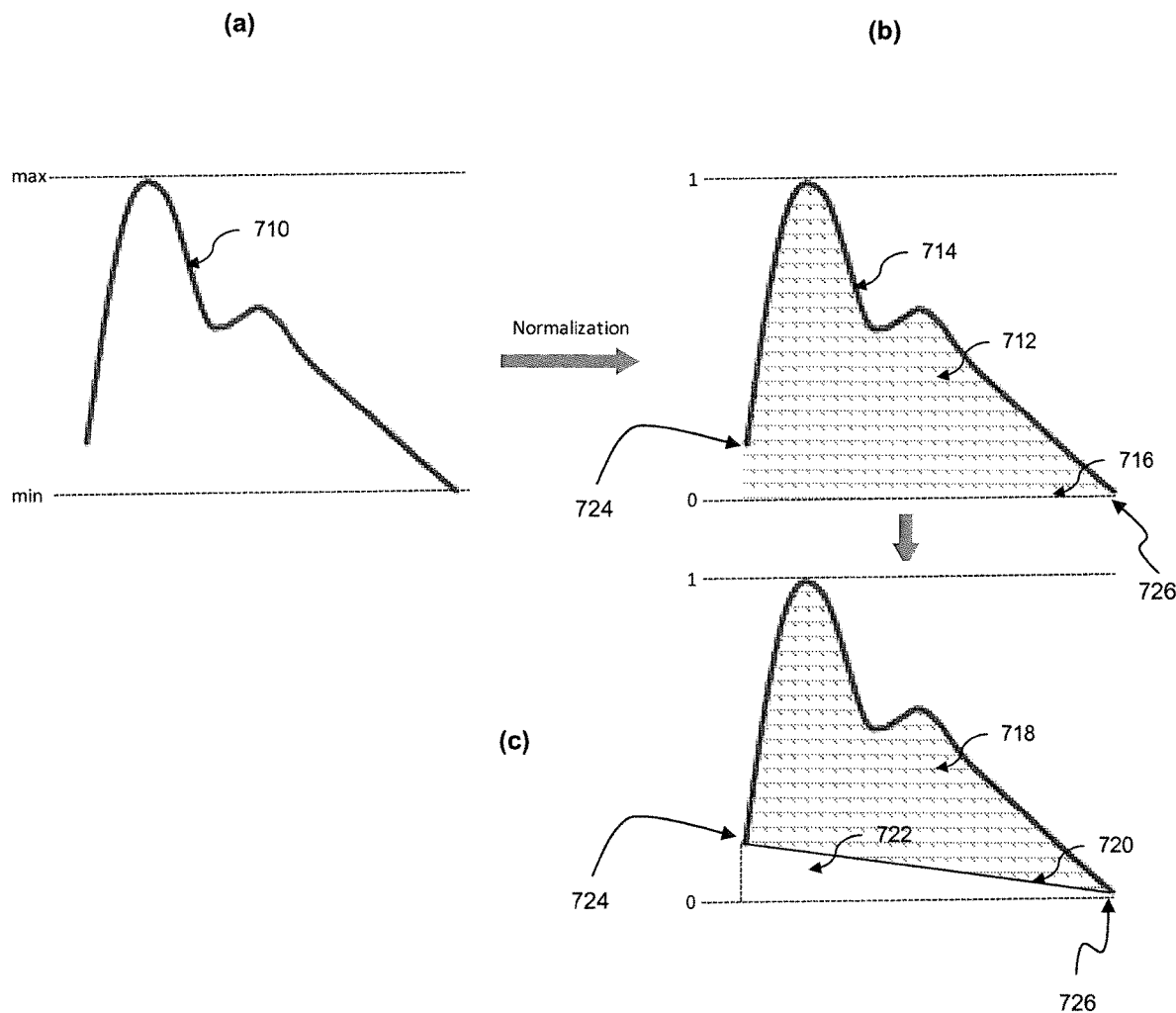
FIG. 6, which includes

FIG. 6a shows another case where a waveform signal 710 (prior to normalization) is not completely bounded by a related time axis 716. FIG. 6b shows the same waveform (which is however labelled as 714 instead to differentiate from FIG. 6a) subsequent to normalization (i.e. normalized waveform 714). An area 712 under the normalized waveform 714 is similarly calculated by the data processing module 114, and the said area 712 is an area relative to the time axis 716. It is to be appreciated that in this instance, the area 712 under the waveform signal 710 is calculated relative to the time axis 716 even though the normalized waveform 714 does not entirely sit on the time axis 716. So the calculated area 712 is to be used as the normalized area. But for better accuracy, a further step may be performed as shown in FIG. 6c, where an area 718 relative to a waveform baseline 720 is calculated by subtracting an outlier area 722 from the area 712 calculated in the step described with respect to FIG. 6b. It is to be highlighted that the outlier area 722 may also be understood as an undesirable/unwanted area. It is to be appreciated that the waveform baseline 720 is drawn to rectilinearly connect a start and an end point 724, 726 of the normalized waveform 714 (as depicted in FIG. 6b), and so the outlier area 722 is thus an area defined between the waveform baseline 720 and time axis 716, which is to be excluded from the area 712 originally computed as per FIG. 6b. That is, the outliner area 722 is in fact not an area strictly enclosed by the normalized waveform 714. In this instance, the outlier area 722 is a triangular area, but is not however to be construed as limiting.

To further enhance an overall accuracy of the measurement result, the data processing module 114 may also be configured to additionally perform a further outlier filtering process to identify and remove outlier normalized areas that are affected by any noise and signal artifacts. Specifically, statistical operations such as calculating the mean, moving average, standard deviation or combinations thereof, may be used by the data processing module 114 to define outlier normalized areas. In an example, normalized areas not within one standard deviation (sigma) derived from all the normalized areas in a measurement window are classified as outliers and will be removed from subsequent calculations.

As above mentioned, it is possible to further enhance the accuracy of the normalized area by determining an average normalized area based on a number of cardiac cycles of the PPG signal 400, instead of using one cardiac cycle. In this case, the average normalized area is subsequently to be used as the normalized area. Specifically, an average normalized area A is calculated based on all the non-outlier normalized areas according to equation (1):

$$A = \text{Sum of all non-outlier areas}/\text{No. of non-outlier areas} \quad (1)$$

That is, an associated area enclosed by each of the cardiac cycles is calculated, and then the average normalized area based on all the calculated associated areas is obtained as the normalized area.

4. Step 208 of the Method

At step 208, the data processing module 114 calculates the heart rate (of the subject 102) within the measurement window using equation (2):

$$HR_n = 60/(TP_{n+1} - TP_n), n \geq 1 \quad (2)$$

in which $TP_{n+1}$ is the time at systolic peak $P_{n+1}$, and $TP_n$ is the time at systolic peak $P_n$. So from equation (2), it is to be appreciated that at least a pair of cardiac cycles that are arranged consecutively together is required for calculation of the heart rate, but is not to be construed as limiting since a number of cardiac cycles of the PPG signal 400 may also be used to improve the accuracy of the heart rate computed. Also, it is to be appreciated that the said systolic peak $P_{n+1}$, and systolic peak $P_n$ are consecutively arranged systolic peaks of the at least a pair of cardiac cycles. In other words, the systolic peak $P_{n+1}$ is the systolic peak of a first cardiac cycle (of the said pair of cardiac cycles), and the systolic peak $P_n$ is the systolic peak of a second cardiac cycle (of the said pair of cardiac cycles). The first and second cardiac cycles are arranged consecutively to each other.

Figure 7:
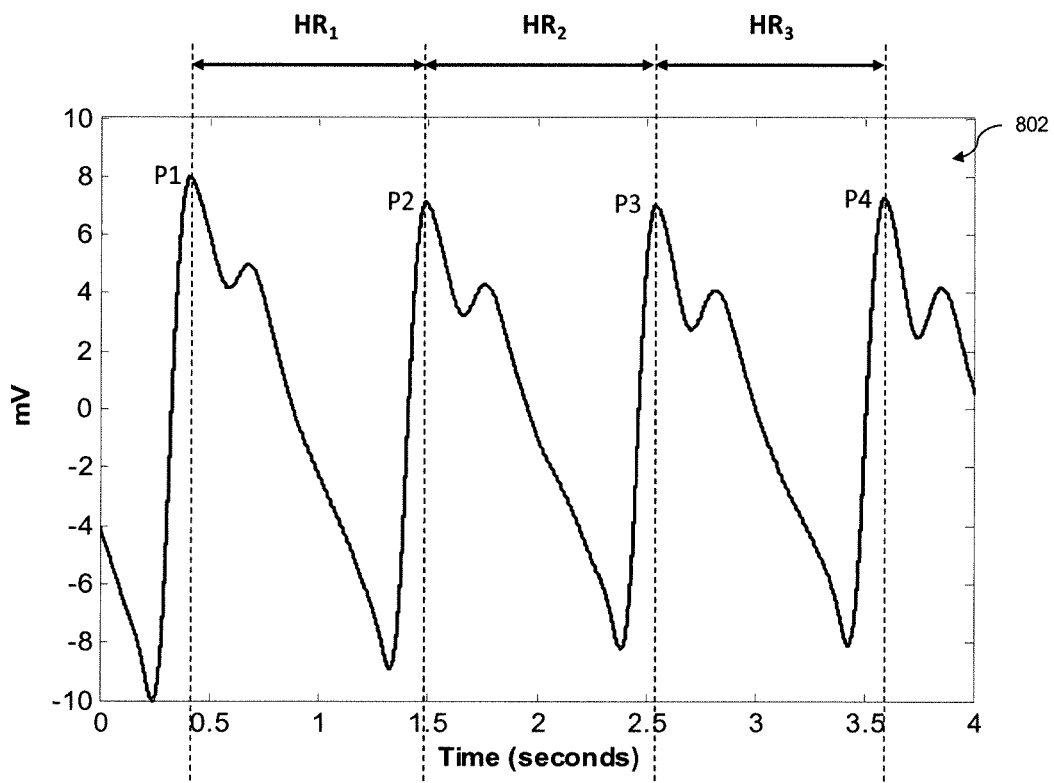
FIG. 7 is a diagram of time intervals measured for the determination of an average heart rate.
Figure 8:
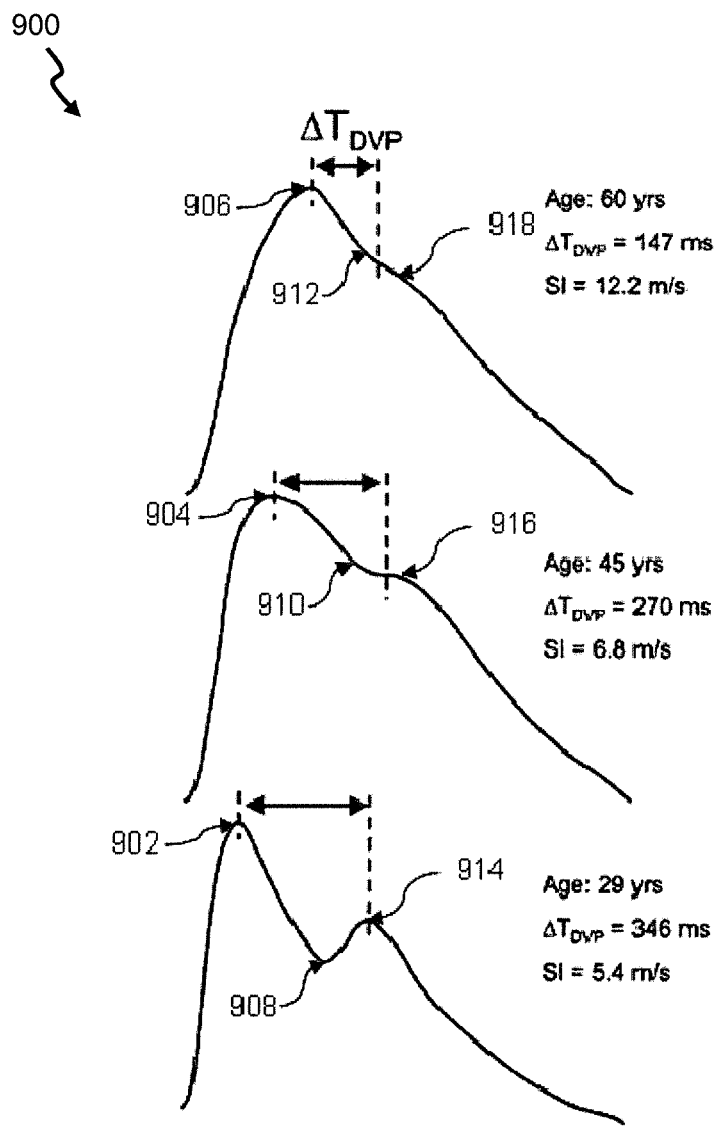
FIG. 8 is a diagram of an arterial waveform, in which effect of age on the diastolic peak and dicrotic notch of the arterial waveform is shown, according to the prior art.

To illustrate, FIG. 7 shows an example in which a heart rate $HR_1$ may be calculated based on a time interval between two systolic peaks $P_1$ and $P_2$ of a PPG signal 802. The time interval between the said systolic peaks $P_1$ and $P_2$ is 1.1 seconds (i.e. 1.5−0.4). So, using equation (2), the heart rate $HR_1$ is calculated as: $HR_1 = 60/(1.5−0.4) = 54.5$. Also, $HR_2$ and $HR_3$ may similarly be calculated as well, in which respectively $HR_2 = 60/(2.6−1.5) = 54.5$ and $HR_3 = 60/(3.6−2.6) = 60.0$.

Likewise to step 206, a similar outlier filtering process is performed to identify and remove outlier heart rates that are affected by any noise and signal artifacts. Thereafter, an average heart rate HR is calculated based on all the non-outlier heart rates, as per equation (3):

$$HR = \text{Sum of all non-outlier heart rates}/\text{No. of non-outlier heart rates} \quad (3)$$

For completeness, for the example in FIG. 7, HR is thus determined as $(54.5+54.5+60.0)/3 = 56.3$.

That is, respective heart rates from respective pairs of the cardiac cycles that are arranged consecutively are calculated, and then an average heart rate based on all the respective heart rates is obtained as the heart rate.

5. Step 210 of the Method

The calculated normalized area and heart rate are (wired/wirelessly) transmitted via the transmission module 116 of the apparatus 100 to the calculation module 124 of the telecommunications device 120 (i.e. received by the receiving module 122). The calculation module 124 calculates the mean arterial pressure (MAP) of the subject 102 based on equation (4):

$$\log(MAP) = b + a_1 \log(A) + a_2 \log(HR) \quad (4)$$

in which A is the average normalized area of an arterial waveform, HR is the average heart rate of the arterial waveform, whereas $a_1$, $a_2$, and b are predetermined coefficients. So equation (4) correlates the calculated average normalized area and average heart rate, each having inherent properties relating to hemodynamic state and cardiovascular functions of the subject 102, to determine the subject's mean arterial pressure.

Of course, it will be appreciated that since the present embodiment is described with reference to the arterial PPG waveform signal 300 (in FIG. 3) comprising at least the pair of cardiac cycles 302, 304, A is then simply the normalized area of the arterial waveform, while HR is the heart rate, as usage of "average" does not qualify in this case because only the at least one of the cardiac cycles 302, 304 is used for the relevant calculations. But if a plurality of cardiac cycles is used, the original definitions of A, and HR provided immediately below equation (4) then apply.

The predetermined coefficients, $a_1$, $a_2$, and b, in equation (4) are obtained empirically, for example using actual clinical data. The clinical data collection may include collecting various different combinations and relationships between features of equation (4), i.e. the MAP, A and HR from test subjects (not shown) involved in the clinical data collection. Determination of the said coefficients, $a_1$, $a_2$, and b, may be performed using a separate computing device (not shown), such as a PC computer, based on any number of optimization algorithms including evolutionary methods, Bayesian statistical methods, or gradient search techniques, as required. In this embodiment, a least square optimization algorithm is used for determining the coefficients, $a_1$, $a_2$, and b. Once the coefficients, $a_1$, $a_2$, and b, are determined, equation (4) is input and stored in the calculation module 124 (of the telecommunications device 120) to be used for any calculation of mean arterial pressure of a subject, without any need for patient-specific calibration procedures.

Figure 10:
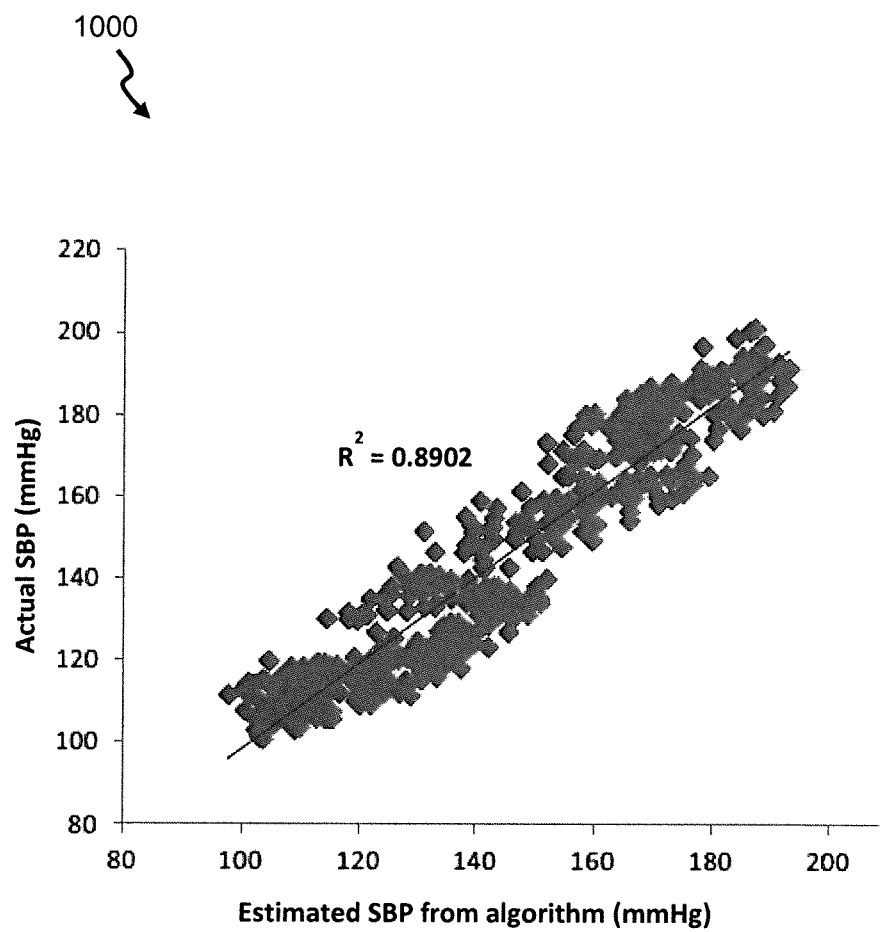
FIG. 10 is a data performance chart related to the apparatus of FIG. 1.

FIG. 10 is a data performance chart 1000 related to the apparatus 100 of FIG. 1.

The remaining configurations will be described hereinafter. For the sake of brevity, description of like elements, functionalities and operations that are common between the different configurations are not repeated; reference will instead be made to similar parts of the relevant configuration(s).

In a second embodiment, equation (4) may alternatively be replaced by equation (5) set out below:

$$\log(MAP)=b+a_1 \log(X_1)+a_2 \log(X_2)+\ldots+a_{n-1} \log(X_{n-1})+a_n \log(X_n) \quad (5)$$

in which $X_1$ to $X_n$ may be values based on: any physiological features of the subject (e.g. such as heart rate, respiratory rate, heart rate variability, blood pressure, pulse pressure etc.), and/or any arterial waveform features (e.g. derived from at least one data point on the waveform, the area under the waveform, frequency value or kurtosis value of the waveform's Power Spectral Density (PSD) graph etc.) which may be derived from the bio-signal. It is to be appreciated that $a_1$ to $a_n$, and b of equation (5) are predetermined coefficients. In this embodiment, the step of normalizing the cardiac cycle waveform signal may be optional, depending on the type of values to be used in any of $X_1$ to $X_n$, since, for example, computing the frequency value/ kurtosis value may not require the said normalization to be performed, while computing the area under the waveform may first require performance of the said normalization (i.e. see step 206 of the first embodiment).

Moreover, further mathematical operations (e.g. addition, subtraction, multiplication, division, power functions, differentiation, integration, normalization, ratios, statistical functions etc.) may also be performed on the said derived features (either individually or in combination with other features) before application into equation (5) for calculation of the MAP.

In a third embodiment, instead of comprising two separate devices, i.e. the optical measurement device 110 and telecommunication device 120, the apparatus 100 itself may be implemented as a single equivalent electronic device, in which the optical measurement device 110 and telecommunication device 120 are (hardware) integrated and configured to perform all the same functions described in the first embodiment. Further, all the steps 202-210 in the flow diagram 200 of FIG. 2 may be implemented as a computer program product downloadable over the internet for storing on a memory of the said electronic device. In other words, if there are improvements to the method of FIG. 2, the electronic device may also be updated (as and when required) with those improvements by way of the downloaded computer program product.

In a fourth embodiment, all the steps 202-210 in the flow diagram 200 of FIG. 2 may be performed by one electronic device which may be the telecommunications device 120 or the optical measurement device 110 (which also be equipped with a display unit). In other words, it is envisaged that the various modules—signal sensing, data processing and calculation modules 112, 114, 124 may form parts of the same electronic device, possibly as part of the optical measurement device 110 or the telecommunications device 120. The single electronic device may also be realised as a wearable sensing device to be worn on the subject's body.

In a fifth embodiment, step 210 of the method in FIG. 2 may be performed by the data processing module 114 of the optical measurement device 110, instead of the calculation module 124 of the telecommunications device 120, if it is determined that the data processing module 114 (for example) has a higher processing power than the calculation module 124, but however not to be construed as a limiting criterion for the data processing module 114 to execute step 210. In addition, performance of step 210 may also dynamically be allocated to the data processing module 114 or calculation module 124 based on a desired arrangement configured by a user of the apparatus 100.

In a sixth embodiment, a pulse pressure (PP) of the subject 102 is further obtained in the method of FIG. 2. A value of the pulse pressure may be self-provided by the subject 102, or automatically measured via a measurement device such as the optical measurement device 110 of FIG. 1, or via using other known suitable devices. Specifically, the pulse pressure of a human is defined as the difference between two important cardiovascular health indicators, i.e. the systolic blood pressure (SBP) and the diastolic blood pressure (DBP). Thus, by utilizing equations (6) and (7) shown below, both blood pressure values, SBP and DBP, of the subject 102 are respectively obtainable as:

$$SBP=MAP+\tfrac{2}{3}PP \quad (6)$$

$$DBP=MAP-\tfrac{1}{3}PP \quad (7)$$

In summary, the proposed method of FIG. 2 advantageously enables measurement of mean arterial blood pressure (MAP) of a subject simply using the arterial waveform of the said subject. Specifically, the proposed method broadly includes the following steps of acquiring a bio-signal having an arterial waveform from the subject's body, identifying respectively the normalized area and heart rate within the bio-signal, and lastly computing the mean arterial pressure based on equation (4) discussed above. Further, the optical measurement device 110 of the apparatus 100, which is arranged to perform the proposed method, is beneficially able to acquire the bio-signal from a single measurement site (of the subject) without requiring an inflatable cuff (unlike conventional solutions), without requiring patient-specific calibration prior to initial use, and further without requiring identification of the dicrotic notch and the diastolic peak of an arterial waveform for analysis.

While the invention has been illustrated and described in detail in the drawings and foregoing description, such illustration and description are to be considered illustrative or exemplary, and not restrictive; the invention is not limited to the disclosed embodiments. Other variations to the disclosed embodiments can be understood and effected by those skilled in the art in practising the claimed invention. For example, in step 206 of the method of FIG. 2, it is instead possible for an associated area enclosed by the cardiac cycle 402 to be first calculated before the calculated area is then normalized to obtain the normalized area.

Figure 9:
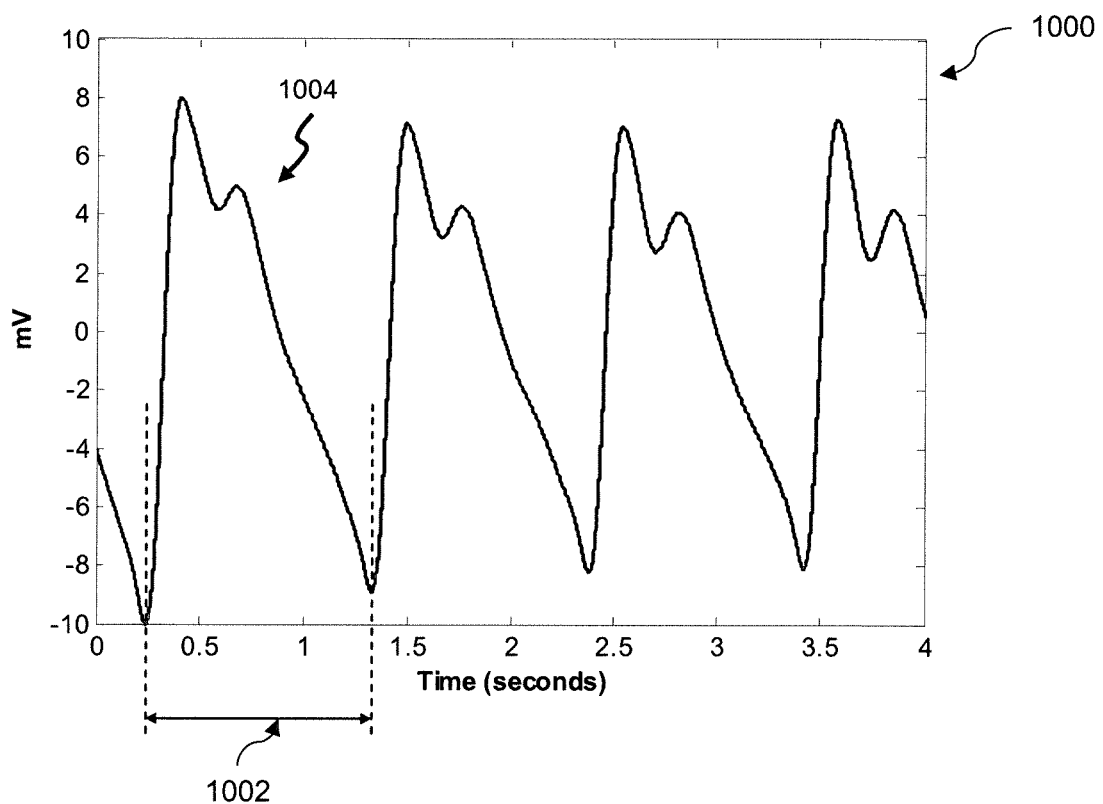
FIG. 9 is a diagram of a time interval measured for the determination of a heart rate, according to a variation.

Also, in step 208 of the method of FIG. 2, the calculation of the heart rate (HR) may alternatively be performed using (associated features of) at least one cardiac cycle, rather than a pair of cardiac cycles. To illustrate, FIG. 9 shows an example in which a heart rate may be calculated based on a time interval 1002 between (for example) two consecutively arranged valleys $V_1$ and $V_2$ of any selected cardiac cycle 1004 of a PPG signal 1000. In this case, the selected cardiac cycle 1004 is a first cardiac cycle of the PPG signal 1000. Specifically, the time interval 1002 between the two valleys $V_1$ and $V_2$ of the selected cardiac cycle 1004 may be used to calculate the HR using equation (8):

$$HR_n = 60/(TV_{n+1} - TV_n), n \geq 1 \quad (8)$$

in which $TV_{n+1}$ is the time at valley $V_{n+1}$, and $TV_n$ is the time at valley $V_n$.

The invention claimed is:
1. A method of deriving mean arterial pressure of a subject, the method comprising:
(i) receiving data from an optical sensor relating to at east one cardiac cycle of a bio-signal from the subject including a waveform signal thereof;
(ii) amplitude-normalizing the received data relating to the at least one cardiac cycle by subtracting a minimum value of the waveform signal from the waveform signal to obtain a subtracted signal, and dividing the subtracted signal by a maximum value of the subtracted signal;
(iii) calculating an area enclosed by the amplitude-normalized received data to obtain an amplitude-normalized area;
(iv) calculating a heart rate of the subject from the at least one cardiac cycle; and
(v) deriving the mean arterial pressure according to the equation:

$$\log(MAP) = b + a_1 \log(A) + a_2 \log(HR)$$

wherein MAP is the mean arterial pressure, A is the amplitude-normalized area, HR is the heart rate, and $a_1$, $a_2$, and b are predetermined constants.

2. A method of claim 1, wherein the data relates to a plurality of cardiac cycles and the method includes amplitude-normalizing respective data relating to each of the cardiac cycles; calculating respective areas enclosed by respective amplitude-normalized data to obtain respective amplitude-normalized areas; and obtaining an average amplitude-normalized area from the calculated amplitude-normalized areas as the amplitude-normalized area.

3. A method of claim 2, wherein the method further includes calculating respective heart rates from respective pairs of the cardiac cycles that are arranged consecutively; and obtaining an average heart rate from the respective heart rates as the heart rate.

4. A method of claim 1, wherein the at least one cardiac cycle includes a pair of cardiac cycles, and wherein calculating the heart rate includes calculating the heart rate according to the equation: HR=60/T, where HR is the heart rate; and
T is a time period determined between respective consecutive systolic peaks of the pair of cardiac cycles that are arranged consecutively.

5. A method of claim 1, wherein calculating the heart rate includes calculating the heart rate according to the equation: HR=60/T, where HR is the heart rate; and
T is a time period determined between respective consecutive valleys of the at least one cardiac cycle.

6. A method of claim 1, wherein calculating the area enclosed by the amplitude-normalized received data includes calculating the area with respect to a time axis which defines the at least one cardiac cycle.

7. A method of claim 1, further comprising:
obtaining pulse pressure of the subject; and
deriving systolic blood pressure and diastolic blood pressure of the subject according to the respective equations: DBP=MAP−(⅓) PP, and SBP=MAP+(⅔) PP,
where MAP is the mean arterial pressure;
DBP is the diastolic blood pressure;
SBP is the systolic blood pressure; and
PP is the pulse pressure.

8. A non-transitory computer-readable medium storing instructions which when executed cause an electronic device to:
(i) receive data from an optical sensor relating to at least one cardiac cycle of a bio-signal from a subject including a waveform signal thereof;
(ii) amplitude-normalize the received data relating to the at least one cardiac cycle by subtracting a minimum value of the waveform signal from the waveform signal to obtain a subtracted signal, and dividing the subtracted signal by a maximum value of the subtracted signal;
(iii) calculate an area enclosed by the amplitude-normalized received data to obtain an amplitude-normalized area;
(iv) calculate a heart rate of the subject from the at least one cardiac cycle; and
(v) derive mean arterial pressure of the subject according to the equation:

$$\log(MAP) = b + a_1 \log(A) + a_2 \log(HR)$$

wherein MAP is the mean arterial pressure, A is the amplitude-normalized area, HR is the heart rate, and $a_1$, $a_2$, and b are predetermined constants.

9. The non-transitory computer-readable medium according to claim 8, wherein the area enclosed by the amplitude-normalized received data is calculated by calculating the enclosed area with respect to a time axis which defines the at least one cardiac cycle.

10. Apparatus for deriving mean arterial pressure of a subject, the apparatus comprising:
(i) a receiver for receiving data from an optical sensor relating to at least one cardiac cycle of a bio-signal from the subject including a waveform signal thereof;
(ii) a processor for:
(a) amplitude-normalizing the received data relating to the at least one cardiac cycle by subtracting a minimum value of the waveform signal from the waveform signal to obtain a subtracted signal, and dividing the subtracted signal by a maximum value of the subtracted signal;
(b) calculating an area enclosed by the amplitude-normalized received data to obtain an amplitude-normalized area;

(c) calculating a heart rate of the subject from the at least one cardiac cycle; and
(d) deriving the mean arterial pressure according to the equation:

$$\log(MAP) = b + a_1 \log(A) + a_2 \log(HR)$$

wherein MAP is the mean arterial pressure, A is the amplitude-normalized area, HR is the heart rate, and $a_1$, $a_2$, and b are predetermined constants.

11. Apparatus of claim 10, wherein the apparatus is in the form of an electronic device.

12. Apparatus of claim 10, wherein the apparatus includes an optical measurement device and a telecommunications device having the receiver; and wherein the optical measurement device includes an optical sensor for obtaining the bio-signal from the subject, and a data processing module for determining data relating to the bio-signal, wherein the receiver of the telecommunications device is arranged to receive the determined data of the bio-signal.

13. Apparatus according to claim 10, wherein the area enclosed by the amplitude-normalized received data is calculated by calculating the enclosed area with respect to a time axis which defines the at least one cardiac cycle.

14. A method according to claim 1, wherein amplitude normalizing the received data relating to at least one cardiac cycle comprises amplitude-normalizing data relating to a single cardiac cycle to obtain amplitude-normalized received data relating to the single cardiac cycle; and
wherein calculating an area enclosed by the amplitude-normalized received data to obtain an amplitude-normalized area comprises calculating an area enclosed by the amplitude-normalized received data relating to the single cardiac cycle to obtain the amplitude-normalized area.

15. A method according to claim 6, comprising calculating an outlier area and subtracting the outlier area from the calculated area to obtain the amplitude-normalized area.

16. A non-transitory computer-readable medium according to claim 9, wherein the instructions when executed cause electronic device to: calculate an outlier area and subtract the outlier area from the calculated area to obtain the amplitude-normalized area.

17. Apparatus according to claim 13, wherein the processor is used for calculating an outlier area and subtracting the outlier area from the calculated area to obtain the amplitude-normalized area.

* * * * *